United States Patent [19]

Molin et al.

[11] Patent Number: 4,659,471

[45] Date of Patent: Apr. 21, 1987

[54] METHOD OF CONTROLLING AN ANAEROBIC TREATMENT PROCESS

[75] Inventors: Nils L. Molin, Lund; Thomas G. Welander, Malmö; Bengt G. Hansson, Hörby; Per-Erik Andersson; Göran E. Annergren, both of Sundsvall, all of Sweden

[73] Assignee: Purac Aktiebolag, Lund, Sweden

[21] Appl. No.: 637,817

[22] Filed: Aug. 6, 1984

[30] Foreign Application Priority Data

Aug. 10, 1983 [SE] Sweden .................................. 8304355

[51] Int. Cl.$^4$ .......................... C02F 3/28; C02F 11/04; C12P 5/02
[52] U.S. Cl. ..................................... 210/603; 210/605; 210/606; 210/614; 210/928; 435/167
[58] Field of Search ............... 210/603, 605, 606, 630, 210/614, 759, 632, 928; 435/262, 801, 167, 264; 48/197 A; 423/586

[56] References Cited

U.S. PATENT DOCUMENTS

| | | | |
|---|---|---|---|
| 1,379,221 | 5/1921 | Scott et al. ........................... | 423/586 |
| 2,429,589 | 10/1947 | Wiley ................................. | 435/801 |
| 3,282,702 | 11/1966 | Schreiner ........................... | 435/262 |
| 3,994,780 | 11/1976 | Klass et al. ........................ | 210/606 |
| 4,022,665 | 5/1977 | Ghosh et al. ....................... | 210/603 |
| 4,067,801 | 1/1978 | Ishida et al. ....................... | 210/603 |
| 4,213,857 | 7/1980 | Ishida et al. ....................... | 210/603 |
| 4,294,703 | 10/1981 | Wilms et al. ....................... | 210/759 |
| 4,461,708 | 7/1984 | Hakulinen et al. ................. | 210/605 |
| 4,491,522 | 1/1985 | Ishida et al. ....................... | 210/605 |
| 4,510,243 | 4/1985 | Haga et al. ......................... | 210/630 |

FOREIGN PATENT DOCUMENTS 2070580 9/1981 United Kingdom ................ 210/632

OTHER PUBLICATIONS

NTIS PB80-124274; "Catalytic Decomposition of Hydrogen Peroxide by Manganese-Alumina"; National Science Foundation (Jan. 1974).

Primary Examiner—Benoit Castel
Attorney, Agent, or Firm—Burns, Doane, Swecker & Mathis

[57] ABSTRACT

The invention relates to a method of treating wastewater from the manufacture of peroxide bleached mechanical or chemi-mechanical pulp. The method comprises a hydrolysis step, a methane fermentation steps and an aerobic step. After the hydrolysis and methane fermentation steps, sludge is separated from the wastewater and partially recycled to the hydrolysis step. The redox potential of the outgoing water from the hydrolysis step is continuously measured and controlled to a value between −400 and −260 mV by regulating the amount of sludge recycled or by passing ingoing wastewater directly to the aerobic treating step.

7 Claims, 3 Drawing Figures

METHOD OF CONTROLLING AN ANAEROBIC TREATMENT PROCESS

BACKGROUND OF THE INVENTION

This invention relates to a method of controlling the treatment of wastewater from the manufacture of peroxide bleached mechanical or chemi-mechanical pulp, which treatment is carried out in at least two anaerobic steps and possibly a subsequent aerobic step. The anaerobic steps are at least one hydrolysis step and a subsequent methane fermentation step.

Wastewater from the manufacture of mechanical pulps contains a relatively high proportion of carbohydrates, which advantageously can be attenuated in an anaerobic step by methane bacteria to methane. In the manufacture of peroxide bleached mechanical or chemi-mechanical pulp, however, the wastewater contains a certain content of hydroperoxide. The methane fermentation step, which contains absolute anaerobic bacteria, does not stand hydroperoxide at all, but the bacteria are killed immediately even at low hydroperoxide concentrations. The methane step, for working satisfactorily, requires that the water ingoing to the methane step do not contain measurable contents of hydroperoxide.

The hydroperoxide content in wastewater from peroxide bleaching of the pulp type in question generally amounts to 0.1-0.3 g/l.

SUMMARY AND OBJECTS OF THE INVENTION

The present invention has, as its primary objective, the controlling of an anaerobic treatment process for the treatment of wastewater from the manufacture of peroxide bleached mechanical or chemi-mechanical pulp.

Briefly described, this as well as other objects not specifically mentioned above are achieved by providing a process comprising a hydrolysis step, a methane fermentation step, an aerobic step, and at least two sludge separation steps. The first sludge separation step is arranged after the hydrolysis step and the second sludge separation step is arranged after the aerobic step. A certain amount of the sludge from the separation steps is partially recycled to the hydrolysis step. This amount is controlled by measuring the redox potential of the outgoing water from the hydrolysis step and maintaining it between a value of $-400$ to $-260$ mV by regulating the amount of added sludge from the sludge separation steps or by passing the ingoing wastewater directly to the aerobic steps. cl BRIEF DESCRIPTION OF THE DRAWINGS FIG. 1 is a flow diagram of the method of the present invention;

DETAILED DESCRIPTION OF PREFERRED EMBODIMENTS

Figure 1:
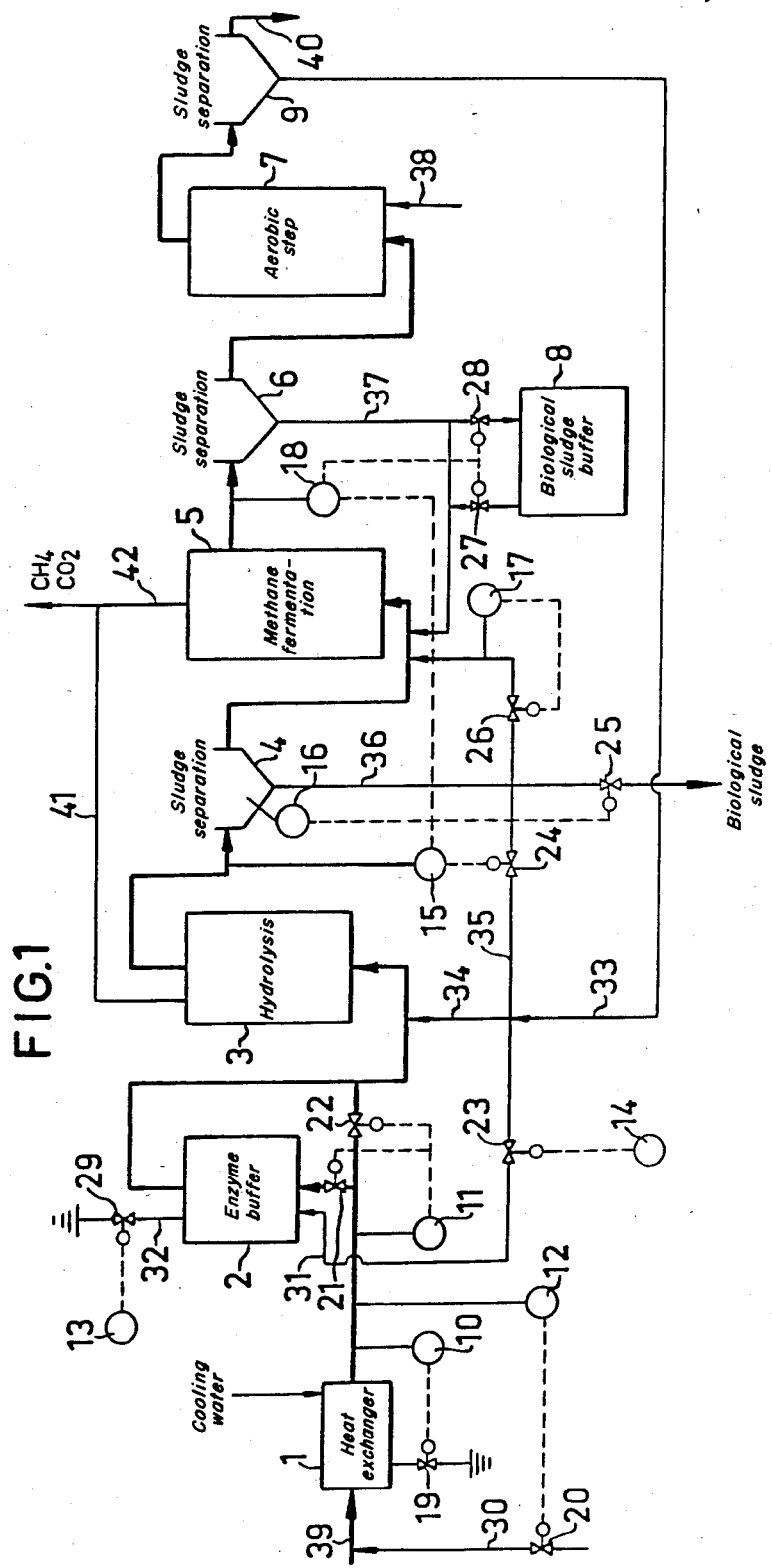

The results of experiments, on which the present invention is based, show that the hydrolysis bacteria of the hydrolysis of water containing peroxide build up a catalase enzyme system, which very efficiently reduces the hydroperoxide content of the water. The redox potential in such an enzyme system provides an understanding of how the catalysis system works. It also is apparent that the redox potential obtained in this system is different of that normally obtained in a hydrolysis step.

In order to ensure that the methane bacteria in the methane step are not knocked out by high peroxide contents, the peroxide decomposition in the hydrolysis step is supervised and controlled by redox measurement and control of the redox potential in the water leaving the hydrolysis step. This is especially important because the generation time for methane bacteria is very long and, therefore, it takes a very long time to build up a new methane bacteria culture.

These investigations have shown that it is possible to treat wastewater from the manufacture of peroxide bleached mechanical or chemi-mechanical pulp containing hydroperoxide in a methane fermentation step to obtain a high methane yield and at the same time to ensure a high and uniform treatment effect. Such is achieved by carrying out a hydrolysis step before the methane step and by supervising and controlling the redox potential of the water which leaves the hydrolysis step and is directed to the methane fermentation step.

The present invention teaches methods of supervising and controlling a treatment plant based on the aforesaid principles, so that the treatment plant biologically never is put out of operation and at the same time is operated in such a manner that an optimum treatment result and an optimum methane yield are obtained.

It was found that heavy metals or heavy metal oxides catalytically can decompose hydroperoxide. Experiments on a laboratory scale have shown that a catalyst pre-step prior to the hydrolysis step containing heavy metals or heavy metal oxide catalyst, for example manganese oxide, efficiently reduce high peroxide contents. By installing a catalyst step prior to the hydrolysis step even very high peroxide contents in ingoing water, exceeding 1 to 1.5 g hydroperoxide/liter, can be managed.

According to the invention, thus, the redox potential of outgoing water from the hydrolysis step shall continuously be measured and controlled to a value between $-400$ mV and $-260$ mV, measured with a platina electrode and with a calomel electrode as reference electrode.

According to a particularly suitable embodiment, the redox potential is maintained in that ingoing water to the hydrolysis step is directed past the hydrolysis step and methane fermentation step to the aerobic step.

The recycling of active biological sludge to the hydrolysis step, further, can be controlled by the redox potential so that an increase of the electrode potential implies an increased recycling of biological sludge to the hydrolysis step. In this case it is suitable to take the increased sludge recycling from a buffer tank with active biological sludge. A certain amount of air can be supplied to this tank.

The electrode potential also can be maintained by recycling sludge from the aerobic step to the hydrolysis step.

It also is advantageous to pass ingoing water to the hydrolysis step through a pre-step containing a catalyst, for example heavy metals.

The invention is described in greater detail in the following by way of some embodiments and with reference to.

EXAMPLE 1

The Example according to FIG. 1 describes a two-step anaerobic fermentation of wastewater from chemi-mechanical pulp manufacture with peroxide bleaching, with a hydrolysis step 3 in a pre-reactor and a methane fermentation step 5 and with a final aerobic treatment step 7. At extreme load with toxic material, an enzyme buffer 2 containing biological sludge can be coupled into the system. Ingoing wastewater, from which disturbing fibre content or the like possibly has been removed, is pH adjusted, for example to pH 6.5, and is cooled in a heat exchanger 1 to a temperature (37° C.) suitable for the treatment.

The redox potential is measured with a platina electrode and with a calomel electrode as reference electrode. When the redox potential exceeds $-300$ mV, the direct line to the pre-reactor 3 is closed/throttled, and the line to the enzyme buffer 2 is opened entirely or partially, which detoxicates the water in proportion to its content of enzyme-containing biological sludge. At loads of long duration or at heavy toxicity shocks the sludge is killed and the buffer loses its detoxicating capacity. The buffer, therefore, is regenerated separately in that the dead sludge is tapped and new active sludge from later steps is filled in during periods when the toxicity of the wastewater is not critical for the process. This toxicity is characterized by the redox signal. The regeneration of the enzyme buffer can be carried out manually or be initiated by a sufficiently low redox signal.

With the water to the pre-reactor follows along biological sludge from the sludge separation directly after the pre-reactor and from the sludge separation after the aerobic step, the sludge of which is recycled entirely or partially in this way. The sludge mixture in question also is used for regenerating the enzyme buffer. The sludge separated after the pre-reactor is divided into three flows. One flow, which is controlled by a redox signal after the pre-reactor with a nominal value of $-400$ mV, is fed-in before the pre-reactor, one flow, which is flow-controlled, is fed-in immediately before the methane fermentation reactor, and one flow, which represents the excess sludge and is controlled by a sludge level measurement at the sludge separation, is removed from the system. The biological sludge from the methane step is recirculated more or less completely. The redox potential is measured after the step and should be $-500$ mV. When a continuous control of this potential is desired, a biological sludge buffer is required which is emptied and, respectively, filled by means of the control system. The control is limited by the size of the buffer and by the requirement of observing the maximum and minimum limits in the buffer.

The redox signal after the methane fermentation step also can be used for a cascade control of previous redox controls. In that case, however, the amplification of the signal must be low so that the long dead time in the process does not induce instability to the control.

The effect of the control primarily is that a high methane yield is ensured. Serious disturbances of the biological material are avoided, disregarding the enzyme buffer, the material of which intentionally is sacrificed in order to avoid serious disturbances later on in the system. Due to the fact that the system produces an excess of sludge, the regeneration of the enzyme buffer should not constitute a serious problem. The regeneration possibly can be made from a sludge buffer, which is built up successively. Measurements of the methane amount, $CH_4/CO_2$-relation in the gas, and pH can be used for trimming the redox nominal values.

Another way of utilizing the invention in very close relationship to this Example is as follows. When the redox potential meter 11 in the Example indicates that the hydroperoxide content in ingoing wastewater to the hydrolysis step is too high, biological active sludge is supplied from the enzyme buffer to the ingoing water to the hydrolysis step in an amount corresponding to the redox potential and thereby to the hydroperoxide content in ingoing water. This is effected in that the valve 21 in FIG. 1 is opened and directs a flow of bacteria sludge from the enzyme buffer to ingoing wastewater. Hereby prerequisite conditions are provided for the redox control after the hydrolysis step to adjust the hydroperoxide content in outgoing water to sufficiently low levels.

EXAMPLE 2

Figure 2:
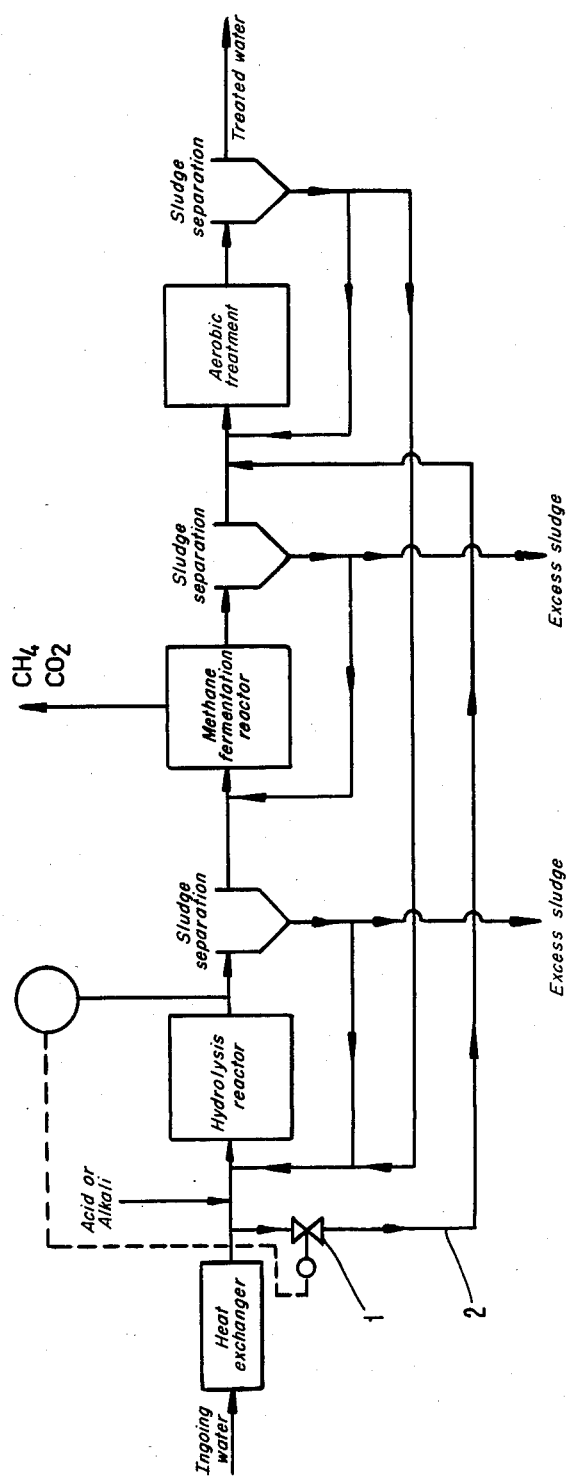
FIG. 2 is a flow diagram of an alternative method of the present invention.

FIG. 2 shows another way of applying the invention. Wastewater from the manufacture of peroxide bleached mechanical or chemi-mechanical pulp is cooled in a heat exchanger to 30°-40° C. Subsequent to the cooling possible nutrient salts and acid or alkali are added so that pH after the hydrolysis reactor is 5.5 to 7. The water is directed to the hydrolysis reactor where the wastewater for about 8 to 20 hours is hydrolyzed bacterially, whereby carbohydrates convert to low molecular organic acids. From the hydrolysis step the water is directed to a sludge separation step where the biological sludge is separated and recycled to the hydrolysis step. The excess of biological sludge is removed from the process.

The water from the hydrolysis step is directed to a methane fermentation step where a great part of the decomposable organic material is converted to methane in known manner. Outgoing water is directed to sludge separation whereafter the sludge is recycled to the methane reactor. The excess sludge is discharged from the process. The water finally passes to an aerobic treatment step, which is provided with an additional sludge separation step. The aerobic sludge is recycled to the aerobic step and/or transferred to the hydrolysis step.

The invention here is applied to such a manner, that the redox potential of outgoing water is measured with a platina electrode and with a calomel electrode as reference electrode. The electrode system is coupled to a regulator, which controls a control valve 1 in the conduit 2. The nominal value of the regulator is set on an electrode potential of the platina electrode of $-360$ to $-350$ mV. When the electrode potential starts exceeding these values, the regulator opens the valve 1 and starts passing part of the ingoing wastewater past the anaerobic steps directly to the aerobic treatment step. The aerobic treatment step contains so much aerobic sludge with enzyme decomposing hydroperoxide, that it withstands the load of hydroperoxide-containing wastewater. In this way the decomposition of hydroperoxide in the hydrolysis step is controlled so that the hydroperoxide content in outgoing water from the hydrolysis step is so low, that the methane fermentation in subsequent steps is not disturbed.

EXAMPLE 3

Figure 3:
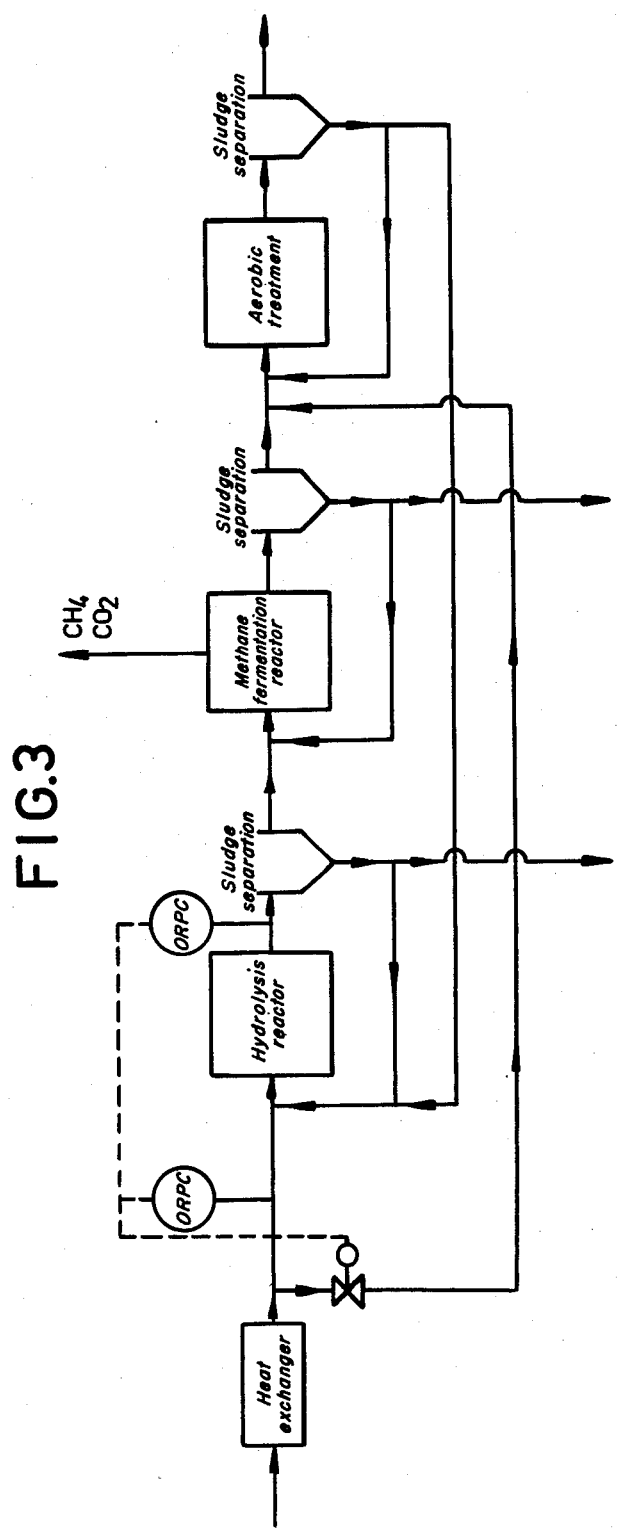
FIG. 3 is a flow diagram of a second alternative method of the present invention.

Another variant of the invention which is closely related to Example 2 is shown in FIG. 3. In order to achieve a faster and safer control, the redox potential in ingoing water is measured, whereby information rapidly is obtained whether the backwater contains high peroxide contents. At very high contents of hydroperoxide in ingoing water, part of the wastewater immediately is directed past the hydrolysis step. The redox potential of the water after the hydrolysis step is measured in the same way as previously. The redox meter can be coupled in cascade with the redox meter for the hydrolysis step in known manner. By this control arrangement a rapid and safe control of the hydrolysis step can be obtained, which yields good optimization of the economy and treatment function of the plant.

The invention is not restricted to the embodiments described, but can be varied within the scope of the invention idea.

We claim:

1. A method of controlling an anerobic treatment process for the treatment of wastewater from the manufacture of peroxide bleached mechanical or chemi-mechanical pulp, comprising the steps of:
   hydrolyzing the wastewater;
   carrying out a methane fermentation of the wastewater;
   aerobically treating the wastewater;
   carrying out at least two sludge separations including separating a first sludge from the wastewater after the hydrolyzing step and separating a second sludge from the wastewater after the aerobic treating step;
   partially recycling an amount of said sludge from at least said first of said at least two sludge separation steps to the hydrolyzing step; and
   continuously measuring and controlling the redox potential of outgoing water from the hydrolyzing step to a value between −400 and −260 mV measured with a platina electrode and with a calomel electrode as reference electrode, the controlling being conducted by regulating the amount of added sludge from the at least two sludge separations or by passing ingoing wastewater directly to the aerobic treating step.

2. The method as defined in claim 1, wherein the sludge recycled to the hydrolyzing step is taken from a buffer tank with active biological sludge.

3. The method as defined in claim 1 further comprising the step of pre-treating wastewater of high toxicity with a catalyst prior to the hydrolyzing step.

4. The method as defined in claim 3, wherein the pre-treating step contains a catalyst for reducing the hydroperoxide content of the water.

5. The method as defined in claim 4, wherein the catalyst comprises one of heavy metals and heavy metal compounds.

6. The method as defined in claim 5 wherein the catalyst is manganese oxide.

7. The method as defined in claim 1 wherein the redox potential of outgoing water from the hydrolysis step is continuously measured and controlled to a value between −375 and −300 mV.

* * * * *